US006566125B2

(12) United States Patent
Johnston et al.

(10) Patent No.: US 6,566,125 B2
(45) Date of Patent: May 20, 2003

(54) USE OF ENZYMES TO REDUCE STEEP TIME AND $SO_2$ REQUIREMENTS IN A MAIZE WET-MILLING PROCESS

(75) Inventors: David B. Johnston, Wyndmoor, PA (US); Vijay Singh, North Wales, PA (US); Steven Eckhoff, Savoy, IL (US)

(73) Assignees: The United States of America as represented by the Secretary of Agriculture, Washington, DC (US); Board of Trustees of the Univ. of Illinois, Urbana, IL (US)

( * ) Notice: Subject to any disclaimer, the term of this patent is extended or adjusted under 35 U.S.C. 154(b) by 0 days.

(21) Appl. No.: 09/871,566

(22) Filed: May 31, 2001

(65) Prior Publication Data

US 2002/0022252 A1 Feb. 21, 2002

Related U.S. Application Data

(60) Provisional application No. 60/208,975, filed on Jun. 2, 2000.

(51) Int. Cl.[7] .............................. C12S 3/12; C08B 30/04
(52) U.S. Cl. ....................... 435/275; 435/267; 435/101; 435/72; 127/65; 127/67; 127/68
(58) Field of Search .......................... 435/101, 72, 267; 435/275; 127/67, 65, 68

(56) References Cited

U.S. PATENT DOCUMENTS

| | | | |
|---|---|---|---|
| 3,900,288 A | 8/1975 | Powell | 127/68 |
| 4,181,748 A | 1/1980 | Chwalek et al. | 426/623 |
| 4,412,867 A | * 11/1983 | Cicuttini | 127/66 |
| 5,959,102 A | 9/1999 | Wasserman et al. | 536/128 |

OTHER PUBLICATIONS

Mahoney, W., et al., "Amino Acid Sequence and Secondary Structural Analysis of the Corn Inhibitor of Trypsin and Activated Hageman Factor", *J. Biol. Chem.*, vol. 259, pp. 8412–8416, 1984.

Krochta, J.M., et al., "Modification of Corn Wet–Milling Steeping Conditions to Reduce Energy Consumption", J. Food Processing, vol. 5, pp. 39–47, 1981.

Watson, S.A., et al., "Peripheral Cells of the Endosperms of Grain Sorghum and Corn and their Influence on Starch Purification", *Cereal Chemistry*, vol. 32, (3), pp. 165–183, May 1955.

Johnston, D.B., et al., "Kinetic Measurements of Cellulase Activity on Insoluble Substrates Using Disodium 2,2'Bicinchoninate", *J. Food Biochem.*, vol. 22, pp. 301–319, 1998.

Chen, Z–Y., et al., "Inhibition of Plant–Pathogenic Fungi by a Corn Trypsin Inhibitor Overexpressed in *Escherichia coli*", *Applied and Environmental Microbiology*, pp. 1320–1324, Mar. 1999.

Abe, M., et al., "Purification and Characterization of a Cysteine Proteinase Inhibitor from the Endosperm of Corn", *Agric. Biol. Chem.*, vol. 52, (6), pp. 1583–1584, 1988.

Maheno–Perez, J., et al., "Effect of Fiber Degrading Enzymes on Wet Milling and Starch Properties of Different Types of Sorghums and Maize", *Starch*, vol. 51, (1), pp. 16–20, 1999.

Doner, L., et al., "An Improved Process for Isolation of Corn Fiber Gum", *Cereal Chemistry*, vol. 75, (4), pp. 408–411, 1998.

Rendleman, C.M., et al., "The Impact of Production Innovations in the Fuel Ethanol Industry", *Agribusiness*, vol. 9, (3), pp. 217–231, 1993.

Eckhoff, S., "Processing/Operational Costs", Presented at the AACC short course on Wet Milling, Jun. 12–15, 2000, Urbana, IL.

Eckhoff, S.R., et al., "Starch Recovery from Steeped Corn Grits as Affected by Drying Temperature and Added Commercial Protease", *Cereal Chemistry*, vol. 68, (3), pp. 319–320, 1991.

Mu–Foster, C., et al., "Surface Localization of Zein Storage Proteins in Starch Granules from Maize Endosperm", *Plant Physiol.*, vol. 116, pp. 1563–1571, 1998.

Spanheimer, J., et al., "Air Classification of Corn Grits. I. Softening Grits with Enzymes and Chemicals", *Cereal Chemistry*, vol. 49, (2), pp. 131–141, Mar.–Apr. 1972.

Abe, M., et al., "Purification and Characterization of a Protease Occuring in Endosperm of Germinating Corn", *Agric. Biol. Chem.*, vol. 41, (5), pp. 893–899, 1977.

Steinke, J.D., et al., "Steeping Maize in the Presence of Multiple Enzymes. I. Static Batchwise Steeping", *Cereal Chem.*, vol. 68, (1), pp. 7–12, 1991.

Steinke, J.D., et al., "Steeping Maize in the Presence of Multiple Enzymes. II. Continuous Contercurrent Steeping", *Cereal Chem.*, vol. 68, (1), pp. 12–17, 1991.

Eckhoff, S.R, et al., "A 100–g Laboratory Corn Wet–Milling Procedure", *Cereal Chem.*, vol. 73, (1), pp. 54–57, 1996.

Lewis, R., "Use of Sulfiting Agents in Food", *Food Additives Handbook*, pp. 412–413, 1989.

Caransa, A., et al., "A Novel Enzyme Application for Corn Wet Milling", *Starch*, vol. 40, (11), pp. 409–411, 1988.

Roushdi, M., et al., "Factors Improving the Steeping Process of Corn Grains", *Starch*, vol. 33, (1), pp. 7–9, 1981.

(List continued on next page.)

*Primary Examiner*—Francisco Prats
(74) *Attorney, Agent, or Firm*—M. Howard Silverstein; John D. Fado; G. Byron Stover

(57) ABSTRACT

A method for obtaining starch from maize involving soaking maize kernels in water to produce soaked maize kernels, grinding the soaked maize kernels to produce a ground maize slurry, and incubating the ground maize slurry with enzyme (e.g., protease).

22 Claims, 10 Drawing Sheets

OTHER PUBLICATIONS

Block, S., "Disinfection, Sterilization, and Preservation", *Automicrobials in Food Sanitation and Preservation*, Fourth Edition, pp. 814–815, 1991.

Lopes–Filho, J.F., et al., "Intermittent Milling and Dynamic Steeping Process for Corn Starch Recovery", *Cereal Chem.*, vol. 74, (5), pp. 633–638, 1997.

D. Jericevic et al., "Influence of the Processing on the Surface Structure of Potato Granules as Viewed by Sem", *Starket*, vol. 29(5), pp. 166–172, 1977.

V. E. Headley et al., "Air Classification of Corn Grits. II. Fine Grinding and Air Classification of Protease–Treated Grits", *Cereal Chem.*, vol. 49, pp. 142–149, Mar.–Apr., 1972.

S.M. Badi et al., "Corn Flour: Reduction of Particle Size", *Cereal Chem.*, vol. 55(4), pp. 489–494, Jul.–Aug., 1978.

M.J. Wolf et al., "Subcellular Distribution and Enzyme Digestibility of Endosperm Proteins of Amylomaize and Normal Corn", *Cereal Chem.*, vol. 52, pp. 771–778, Nov.–Dec., 1975.

F. Berkhout, "The Manufacture of Maize Starch", IN: *Starch Production Technology*, Radley, J.A. eds., Applied Science Publishers: Essex, England, pp. 109–133, 1976.

"The Manufacture of Corn Starch", IN: *Chemistry and Industry of Starch*, Kerr, R. W., eds., Academic Press: New York, N.Y., pp. 29–61, 1950.

P. H. Blanchard, "Technology of Corn Wet Milling and Associated Processes", *Industrial Chemistry Library*, vol. 4, Chapter 3, Elsevier: New York, NY, pp. 69–86, 1992.

R.A. Anderson, "Corn Wet Milling Industry", IN: *Corn Culture, Processing Products*, Inglett, G.E. eds., AVI Publishing Company: Westport, CT, pp. 151–170, 1970.

S.A. Watson, "Corn and Sorghum Starches: Production", *Starch*, Academic Press, $2^{nd}$ Ed., Chapter XII, pp. 417–467, 1984.

J.B. May, "Wet Milling: Process and Products", IN: *Corn: Chemistry and Technology*, Chapter 12, pp. 377–397.

R.J. Alexander, "Corn Dry Milling: Processes, Products, and Applications", IN: *Corn: Chemistry and Technology*, Chapter 11, pp. 351–376.

R.C. Hoseney, "Dry Milling of Cereals", IN: *Principles of Cereal Science and Technology*, Chapter 6, $2^{nd}$ Ed., pp. 125–145.

R.C. Hoseney, "Wet Milling: Production of Starch, Oil, and Protein", IN: *Principles of Cereal Science and Technology*, Chapter 7, $2^{nd}$ Ed., pp. 147–158.

* cited by examiner ial Application No. 60/208,975, filed Jun. 2, 2000, which is incorporated herein by reference in its entirety.

USE OF ENZYMES TO REDUCE STEEP TIME AND SO₂ REQUIREMENTS IN A MAIZE WET-MILLING PROCESS

REFERENCE TO RELATED APPLICATION

This application claims the benefit of U.S. Provisional Application No. 60/208,975, filed Jun. 2, 2000, which is incorporated herein by reference in its entirety.

BACKGROUND OF THE INVENTION

The present invention relates to a method for obtaining starch from maize (corn) involving soaking maize kernels in water to produce soaked maize kernels, grinding the soaked maize kernels to produce a ground maize slurry, and incubating the ground maize slurry with enzyme (e.g., protease).

To meet the expanding needs for ethanol and to be competitive with other petroleum based oxygenate additives, ethanol production costs must be lowered and the value of co-products increased. Approximately 60–70% of ethanol in the U.S. is produced by the conventional corn wet-milling process. The wet-milling process separates corn (maize) into a pure starch product and co-products rich in oil, fiber and protein. The corn is initially hydrated (steeped) in an aqueous solution of sulfur dioxide. The steeped corn is coarsely ground to loosen the intact germ from the kernel. Since germ contains a high concentration of oil (~45%), it is lighter than the other constituents of the ground slurry and can be separated (by density difference) by use of germ hydrocyclones. The remaining slurry is finely ground to disrupt the endosperm matrix and release the starch particles. Fiber particles are removed by passing the slurry over fine screens (75 μm openings). Starch is separated from protein in a system of centrifuges and hydrocyclones, resulting in a starch fraction containing less than 0.35% (d.s.) protein. Starch is then further processed for different products such as ethanol or corn syrups.

The first and most important operation in the corn wet-milling process is steeping. Steeping involves soaking corn kernels counter-currently for 24–48 hours in warm (48°–54° C.) sulfurous (0.1–0.2%) water. The purpose of steeping is to soften the corn kernel and to break the disulfide bonds holding the protein matrix together. Steeping is a diffusion limited process. The water and the steep chemicals (generally 2000–2500 ppm $SO_2$ and 0.5–2% lactic acid (usually produced during steeping by lactobacillus bacteria)) diffuse into the corn kernel through the base end of the tip cap, move through the cross and tube cells of the pericarp to the kernel crown and into the endosperm. The $SO_2$ in the endosperm reacts with the protein matrix that encapsulates the starch granules. The result is dispersion of endosperm protein and an enhancement of starch release during subsequent milling (Watson, S. A., et al., Cereal Chem., 38:22–23 (1961)). The penetration of $SO_2$ into the endosperm and its reaction time with the protein matrix makes steeping a very time consuming operation (24 to 36 hours) in the corn wet-milling process. Steeping times shorter than 24 hours result in poor starch yields and loss of starch to fiber and protein fractions. Steeping is also one of the most capital and energy intensive parts of the corn wet-milling process. It is estimated that 21% of the total energy and capital cost is used for the steeping operation (Eckhoff, S. R., Wet milling short course, Course Notes, American Association of Cereal Chemists, St. Paul, Minn., 1999). Reducing steep time would decrease energy cost, increase plant capacity and reduce the capital cost involved in construction of new corn wet-milling plants.

Several mechanical and chemical approaches have been investigated to decrease steep time while maintaining product yields. These processes, however, required costly modifications of existing facilities or pretreatment of kernels, resulting in increased pollution or increased energy use (U.S. Pat. No. 3,597,274; Roushdi, M., et al., Starch/Stärke, 33: 7–9 (1981); Krochta, J. M., et al., J. Food Process. Preserv.,. 5: 39 (1981); Meuser, F., et al., 1985, The use of high-pressure disintegration technique for the extraction of starch from corn, pages 161–180, IN: New Approaches to Research on Cereal Carbohydrates, R. D. Hill and L. Munck, eds., Elsevier, Amsterdam; Hassanean, A., and A. Abdel-Wahed, Starch/Stärke, 38: 417 (1986); Grindel, R. S., Starch/Stärke, 17: 298 (1965); Neryng, A., and P. J. Reilly, Cereal Chem., 61: 8 (1984)).

The development of a processing procedure that could reduce the steep time and decrease or eliminate the use of chemicals such as sulfur dioxide would have a significant impact on the corn wet-milling industry. Such a process would appreciably decrease operational energy costs, increase plant capacity and reduce the capital costs involved in the construction of new corn wet-milling facilities.

SUMMARY OF THE INVENTION

A method for obtaining starch from maize involving soaking maize kernels in water to produce soaked maize kernels, grinding the soaked maize kernels to produce a ground maize slurry, and incubating the ground maize slurry with enzyme (e.g., protease).

DETAILED DESCRIPTION OF THE INVENTION

Figure 1:
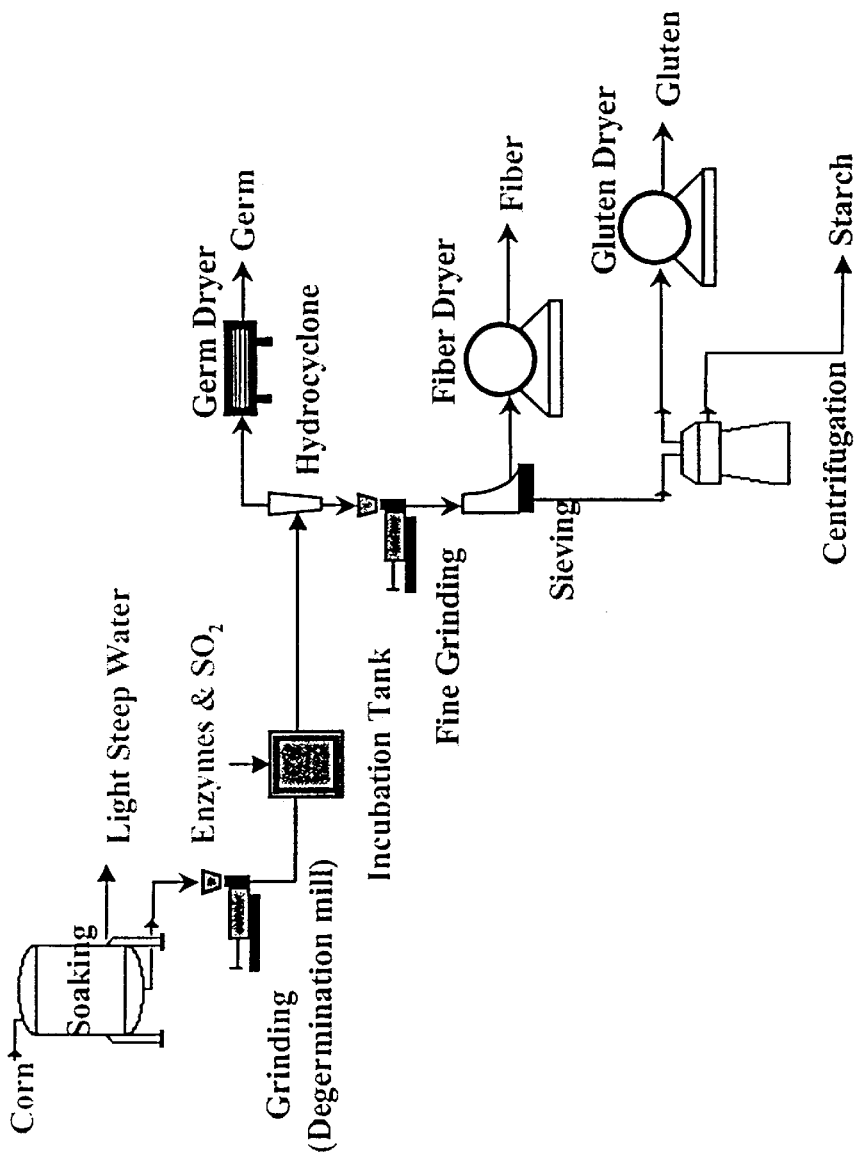
FIG. 1 shows a general flow diagram showing the overall corn wet milling process with the addition of the new enzyme incubation step.

The present invention involves hydrating the corn kernel in water for 1–6 hours so that the germ is completely hydrated and becomes pliable enough that it does not break when the corn is coarsely ground; coarsely grinding the corn to produce a slurry; and treating the coarsely ground corn slurry with exogenous or endogenous enzyme (e.g., protease) for 0.5–6 hours. After enzyme (e.g., protease) treatment, the corn will be milled using the normal corn wet-milling methods. The present approach removes the diffusion barriers and allows the enzymes to penetrate inside the corn endosperm and react with the protein substrate. The overall steeping time with the modified procedure will generally range from 6 to 8 hours. A general flow diagram showing the overall process is shown in FIG. 1.

The corn kernels are hydrated (soaked) in water, generally for about 1-about 6 hours (e.g., 1–6 hours), preferably about 2-about 4 hours (e.g., 2–4 hours), more preferably about 3 hours (e.g., 3 hours), and at a temperature of about 45° to about 60° C. (e.g., 45°–60° C.), preferably about 48° to about 52° C. (e.g., 48°–52° C.), preferably about 45° to about 50° C. (e.g., 45°–50° C.), more preferably about 48° C. (e.g., 48° C.).

The hydrated corn kernels are then coarsely ground to form a ground corn slurry. After initial hydration corn will be normally ground using a degermination mill (particle reduction device commonly used in corn wet-milling industry) or similar equipment. Degermination mills are usually equipped with one fixed and one rotating Devil's tooth plate which mesh closely and are designed specifically for corn. Mill plates can be adjusted for gap settings. The plate gap setting and the rpm of the mill controls the impact and shearing force on the kernels and, therefore, affects the quality of germ recovered. Initial hydration of corn is done to get enough water in the corn kernel so that the germ will not break when corn is ground using a degermination mill. In the present invention, generally a little bigger gap is used between the mill plate (than usually used by the corn wet-milling industry) to do the coarse grind (coarse grind in wet-milling industry is also known as first grind); although using the normal gap setting (as used by corn wet-milling industry) will not significantly affect the germ recovery.

The ground corn slurry is incubated with enzyme (e.g., protease), generally for about 0.5-about 6 hours (e.g., 0.5–6 hours), preferably about 1-about 4 hours (e.g., 1–4 hours), more preferably about 3 hours (e.g., 3 hours), and at a temperature of about 20° to about 70° C. (e.g., 20°–70° C.), preferably about 40° to about 55° C. (e.g., 40°–55° C.), more preferably about 48° C. (e.g., 48° C.). The temperature can be changed depending on the specific enzyme used, but would not go above the gelatinization temperature of about 70° C. or above the thermal stability of the enzyme. The enzymes used in the first set of examples were proteases (specifically Bromelain from Pineapple stem purchased from Sigma, the amount of enzyme varied but was from 250 mg to 1 g of enzyme per 100 g of corn; or other enzymes with similar activity as Bromelain). It is within the skill of one skilled in the art to optimize the amount of enzyme. The incubation time can be increased so less enzyme can be used.

It is also within the skill of one skilled in the art to determine which proteases can be successfully utilized in the present invention; for example, there is a protease in the corn kernel that may be useful in the release of starch granules. Selection of other enzymes that could be used in this process would need to consider activity and stability under the specific conditions used. Such enzymes would need to have the ability to hydrolyze the proteins surrounding the starch granules. As a result, enzymes would be selected that have specificity toward peptide linkages in glutelins and zein (and more minor) corn endosperm proteins. Resulting peptides would then be separated during processing. The reaction conditions would need to consider enzyme concentration, pH, temperature, sulfur dioxide tolerance (if used), and other enzyme specific factors such as mineral or cofactor requirement.

After incubation with enzyme (e.g., protease)), the corn is ground and degermed (germ is removed). The remaining slurry is further ground (finely) and then sieved to remove fiber. The rest of the material (starch and protein) is separated using hydrocyclone (separation based on density difference) or other similar equipment. Generally, wet-milling conditions after steeping with or without enzymes would be same as used by corn wet-milling industry.

The following examples are intended only to further illustrate the invention and are not intended to limit the scope of the invention as defined by the claims.

EXAMPLES

First Set of Examples:

Corn (100 g) was initially soaked in water (180 mL) for 3 hours at 48° C. and the soak water removed (can be done from 1.0–6.0 hours at 45–60° C.). The corn was then ground using a Waring type blender in an equal volume of water to simulate the normal first grind (coarse grind) as commonly done in the wet milling industry.

To the slurry was added normal steeping chemicals (sodium metabisulfite at 600–2000 ppm with or without lactic acid (0.5% w/w)) or sodium acetate buffer, pH 4.0, to a final concentration of 0.05 M. Enzyme was then added to the slurries (500 mg of Bromelain from pineapple stem was used for results shown in FIGS. 2 and 3 but other enzymes were tested) and the slurry incubated for 1–4 hours at 48° C. (can be done from 0.5–6.0 hours at 20–70° C.) with stirring every 30 min. (can be stirred continuously).

Following the incubation period, the slurry was processed according to the procedure of Eckhoff et al. (Eckhoff, S. R., et al., "A 100-g laboratory corn wet-milling procedure", Cereal Chem. 73:54–57 (1996)) to determine the fraction yields (fiber, starch, germ, and protein).

Protein content of the starch was determined using AOAC 991.201 Official Methods of Analysis (Association of Official Analytical Chemists, Washington, D.C). Values shown are the average of duplicate measurements.

Figure 2:
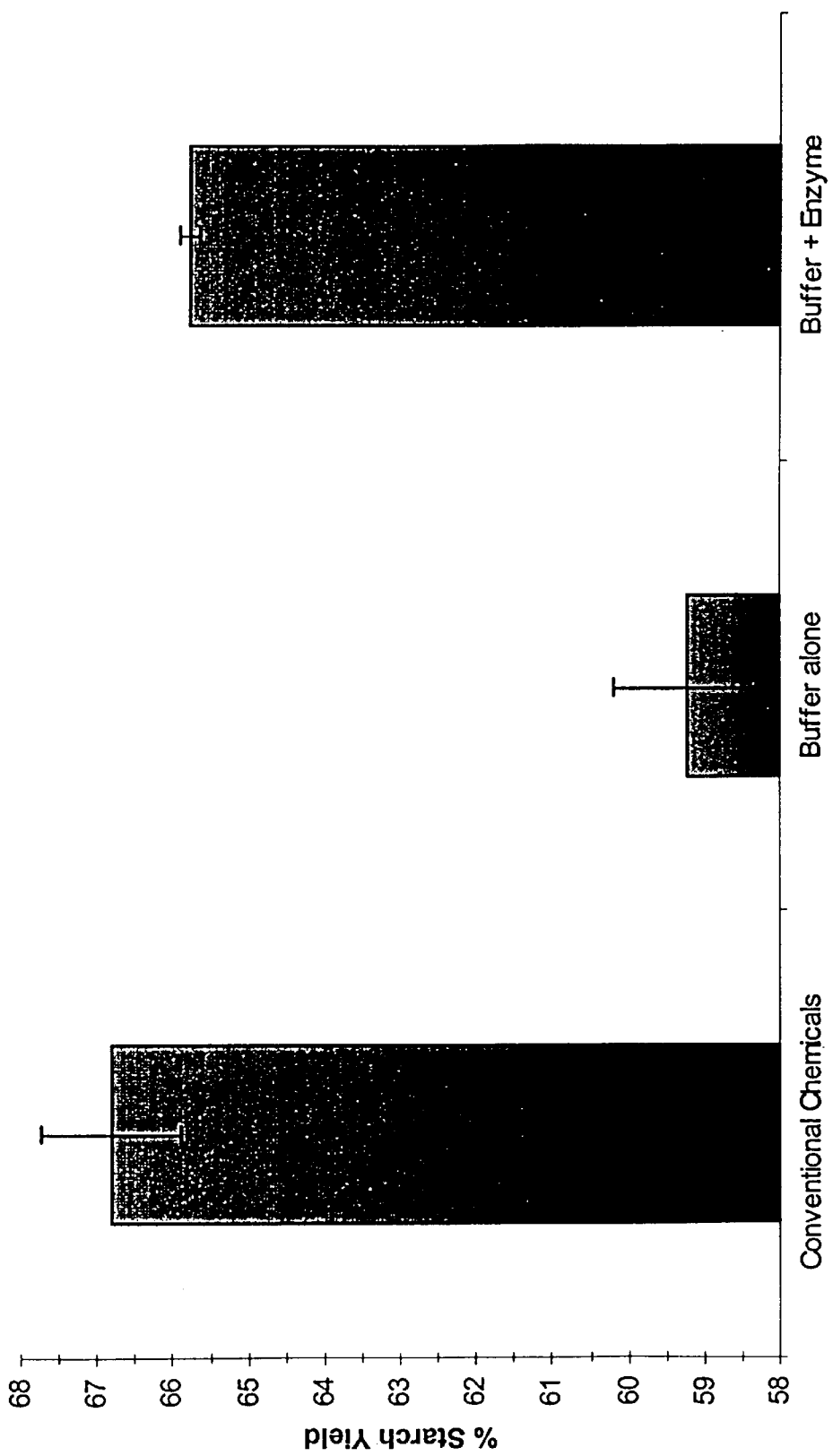
FIG. 2 shows a comparison of starch yields from corn samples steeped using the two step procedure with conventional steeping chemicals ($SO_2$ and lactic acid), in buffer alone, and enzymatically (buffer+enzyme), error bars represent±one standard deviation from a duplicate average.

Results in our laboratory have shown that proteases (with no steep chemicals added), when used with the modified two step steeping procedure, showed significant improvement in starch yields over water steeped samples and had yields comparable to conventionally steeped samples (steeped with $SO_2$ and lactic acid)(FIG. 2). This is in sharp contrast to the use of the same enzymes in a single step steeping procedure where there is no significant improvement over controls.

Additional studies have shown that maintaining the same level of enzyme and increasing the incubation time gives starch yields equivalent to conventionally steeped samples. We have also demonstrated that these enzymes can be used in the presence of $SO_2$ and that the starch yields using a significantly reduced concentration of $SO_2$ (600 ppm) are indistinguishable from the conventional controls (2000 ppm) (FIG. 3). 2000–2500 ppm of $SO_2$ is normally used commercially. One purpose of using $SO_2$ is to control the microbial content in different product streams, microbes can be controlled by using as little as 600 ppm of SO2. The enzyme was not inactivated by 600 ppm of $SO_2$.

The protein content of the starch shows that the enzyme treated samples, (with or without $SO_2$) have similar protein content to the conventionally steeped samples. The control sample without $SO_2$ and without enzyme shows a significantly higher protein content.

Second Set of Examples:

Protease enzymes (bromelain from pineapple stem; pepsin from porcine stomach mucosa; Aspergillus acid proteinase, Type XIII from *Aspergillus saitoi*) were purchased from Sigma. All other enzymes (xylanase, cellulase, cellobiase, β-glucanase) were supplied as gifts from manufacturers. A yellow dent corn hybrid (Pioneer 3394 grown during the 1999 crop season at the Agricultural Engineering Farm, University of Illinois at Urbana-Champaign) was used for the study. Corn samples were hand cleaned to remove broken kernels and foreign materials. Samples were then packaged and stored at 4° C. until used. The whole kernel moisture content of the samples was measured using the 103° C. convection oven method AACC 2000a (American Association of Cereal Chemists (AACC), 2000a, Approved Methods of the AACC, 8th ed., Method 44-15A, The Association: St Paul, Minn.).

Enzyme Activity Measurements:

Protein content was determined by the Bradford method (Bradford, M. M., Anal. Biochem., 72: 248–254 (1976)) with reagents purchased from Sigma, using Bovine Serum Albumin as the protein standard. The carbohydrase activities were measured as an increase in reducing groups equivalents in acetate buffer, pH 4.5 at 40° C. (Johnston, D. B., et al., J Food Biochem, 22: 301–319 (1998)); activity units were defined as the change in reducing groups, equivalent to an increase of 1 μg sugar per min. The cellulase and β-glucanase assays used carboxymethyl cellulose and barley β-glucan as substrates, respectively, and glucose as the standard sugar. The xylanase and hemicellulase assays used xylan and corn fiber gum (Doner, L. W., et al., Cereal Chem., 75: 408–411 (1998)) as substrates, respectively, and xylose as the standard sugar. The amylase and native starch assays used gelatinized and ungelatinized corn starch as substrate and maltose as the standard sugar. Protease activity was done according to the modified method of Anson (Abe, M., et al., Agric. Biol. Chem., 41(5): 893–899 (1977)); one protease unit is defined as the $\Delta A_{280}$ of 0.001 per min (1 cm light path) at pH 4.5 and 40° C., measured as TCA soluble products using hemoglobin as substrate in the presence of 10 mM cysteine.

Wet-Milling Procedures:

Conventional corn wet-milling was done using the 100 g laboratory corn wet-milling procedure (Eckhoff, S. R., et al., Cereal Chem., 73: 54–57 (1996)). The two-stage modified steeping procedure was conducted as follows: Samples of corn (100 g) were placed in 500 mL Erlenmeyer flasks with 180 mL of water or steeping chemicals (0.2% $SO_2$+0.55% lactic acid). The corn was soaked for 3 h at 48° C. The water was drained into a 250 mL graduated cylinder and this unabsorbed water volume was measured and then dried to determine total solids using the two stage drying procedure AACC 2000b (American Association of Cereal Chemists (AACC), 2000b, Approved Methods of the AACC, 8th ed., Method 44-18, The Association: St Paul, Minn.). The corn was then milled in an equal volume of water (v/v) using a Waring type blender. The slurry was then transferred to an Erlenmeyer flask and additional reagents added (enzyme, buffer, sodium metabisulfite, lactic acid). The flask was then incubated at 48° C. (water bath) for the 1–4 h, with mixing at 30 min intervals. After incubation, the slurry was milled with the conventional wet-milling laboratory procedure (Eckhoff, S. R., et al., Cereal Chem., 73: 54–57 (1996)).

Incubation Conditions:

Normal steeping was done using the unmodified 100 g procedure (Eckhoff, S. R., et al., Cereal Chem., 73:54–57 (1996)) using 2000 ppm sulfur dioxide and 0.55% lactic acid and steeping for 24 h at 52° C. prior to milling. Enzymes and chemicals were added directly to the steeping solution. Enzyme treatments were done with the addition of sulfur dioxide and lactic acid, with only lactic acid, and with no chemicals. Steeping times other than 24 h were also tested.

Normal two-stage steeping was done using 2000 ppm sulfur dioxide with 0.55% lactic acid added during the initial soaking step (3 h). No additional chemicals were added during the second incubation procedure.

Enzyme treated samples using the two-stage procedure were soaked in water (no steeping chemicals, enzymes or buffer) for the first step of the process. Following the first grind, 10 mL of 1 M sodium acetate buffer, pH 4.0, was added to control pH (the final pH was 4–4.5). Sodium metabisulfite was added to the indicated samples to give a sulfur dioxide equivalent concentration of 200, 600 or 2000 ppm. Enzymes were added either as a dry powder (bromelain, 250, 500 or 1000 mg; pepsin, 250 mg; Aspergillus acid proteinase Type XIII, 250 mg) or as liquid (cellulases, xylanases, or β-glucanase, 5 mL). Control (buffer) and sulfur dioxide only treated samples were done identically but without any enzyme addition.

Protein Assay of Starch:

Protein content of the starch was determined by a commercial analytical laboratory (Silliker Laboratories Group, Chicago Heights, Ill.) using AOAC method 991.20 (AOAC Official Methods of Analysis, 1990, revised March 1996, Nitrogen (Total) in milk, method 991.20, AOAC 73, 849).

Results of Conventional (One-Step) Procedure with Enzyme Treatments:

The initial experiments were intended to replicate the published results for enzymes added during conventional steeping (Steinke, J. D., and L. A. Johnson, Cereal Chem., 68: 7–12 (1991); Caransa, A., et al., Starch/Stärke, 40: 409–411 (1988); Hassanean, A., and A. Abdel-Wahed, Starch/Stärke, 38: 417 (1986); Moheno-Perez, J. A., et al., Starch, 51: 16–20 (1999)) using the highly reproducible 100 g laboratory corn wet milling procedure. Experimental treatments consisted of enzyme addition with the following: (a) addition of sulfur dioxide and lactic acid, (b) addition of lactic acid without sulfur dioxide, and (c) without addition of sulfur dioxide or lactic acid. The 24 h steeping experiments showed no improvement in starch yield with the addition of any of the enzyme combinations tested. A small but statistically significant decrease in starch yields compared to buffered controls was observed with several samples.

Figure 5:
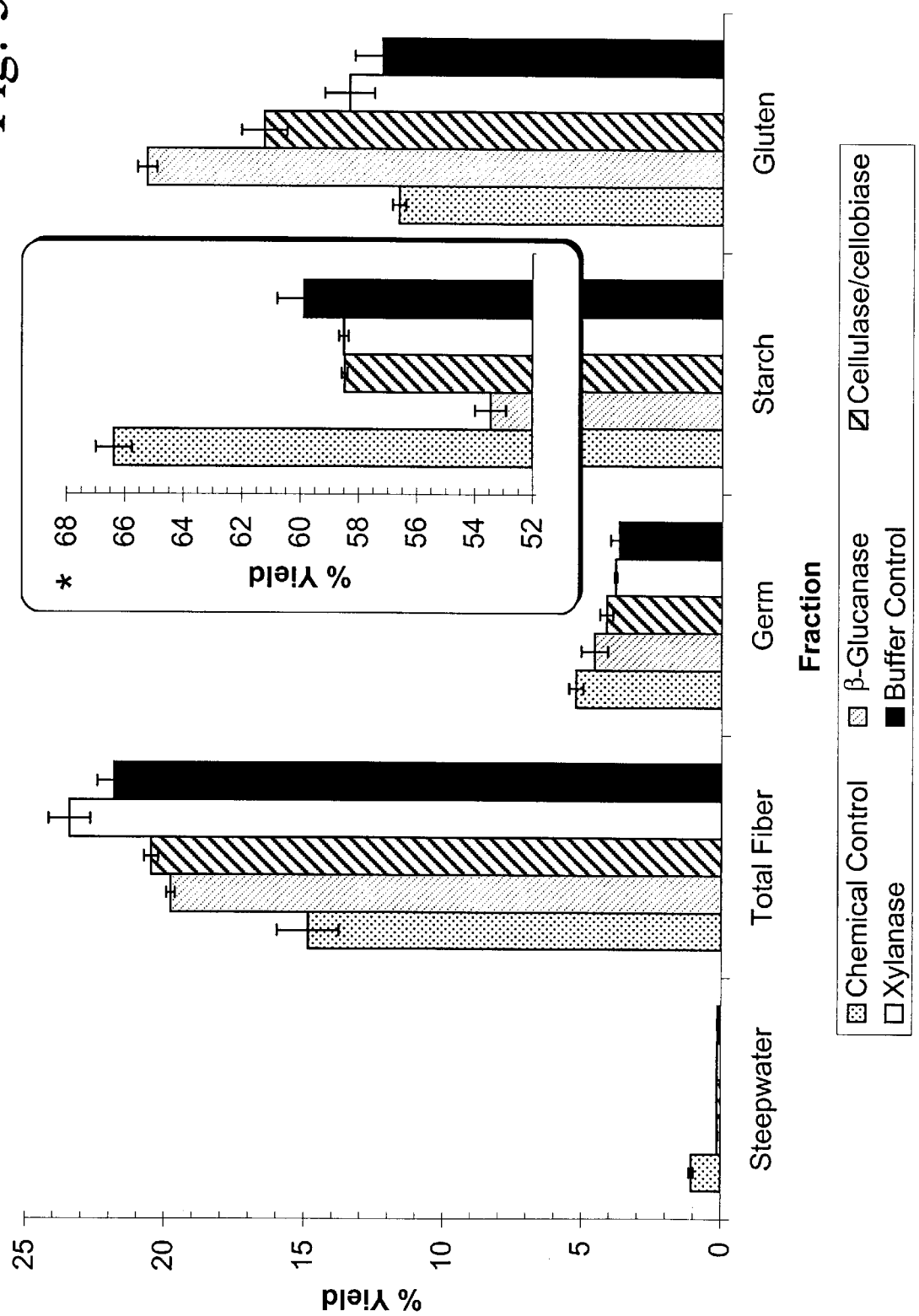
FIG. 5 shows a comparison of fraction yields from corn samples steeped using individual hydrolase preparations, normal chemicals (chemical control; $SO_2$ at 2000 ppm and 0.55% lactic acid) and buffer alone (buffer control; 0.05 M acetate buffer, pH 4.0); error bars represent±one standard deviation from a duplicate average (quadruplicate for controls); the scale for the inserted graph is different from the scale used in FIGS. 6–9.

Results of Two-Stage Procedure with Glycosidases:

When the two-stage modified procedure was used (3 h soak of intact kernels followed by coarse grinding and a 3 h incubation of the ground slurry) with enzyme preparations similar to those used in the conventional (one-step) procedure, significant increases as well as decreases were observed for starch yields. The mixtures of commercial preparations showing decreased starch yields were further tested to identify the specific component responsible. FIG. 5 shows the fraction yields for three individual components (β-glucanase, cellulases or xylanases). Although all three showed a significant decrease in starch yields when compared to the buffer control starch yield, the β-glucanase preparation was clearly identified as being the major component responsible for the extensive decrease in starch yields. The gluten yields were also elevated for the β-glucanase preparation, potentially indicating a loss of starch through enzymatic hydrolysis into the gluten fraction. None of the carbohydrases tested were helpful in increasing starch yields.

Figure 6:
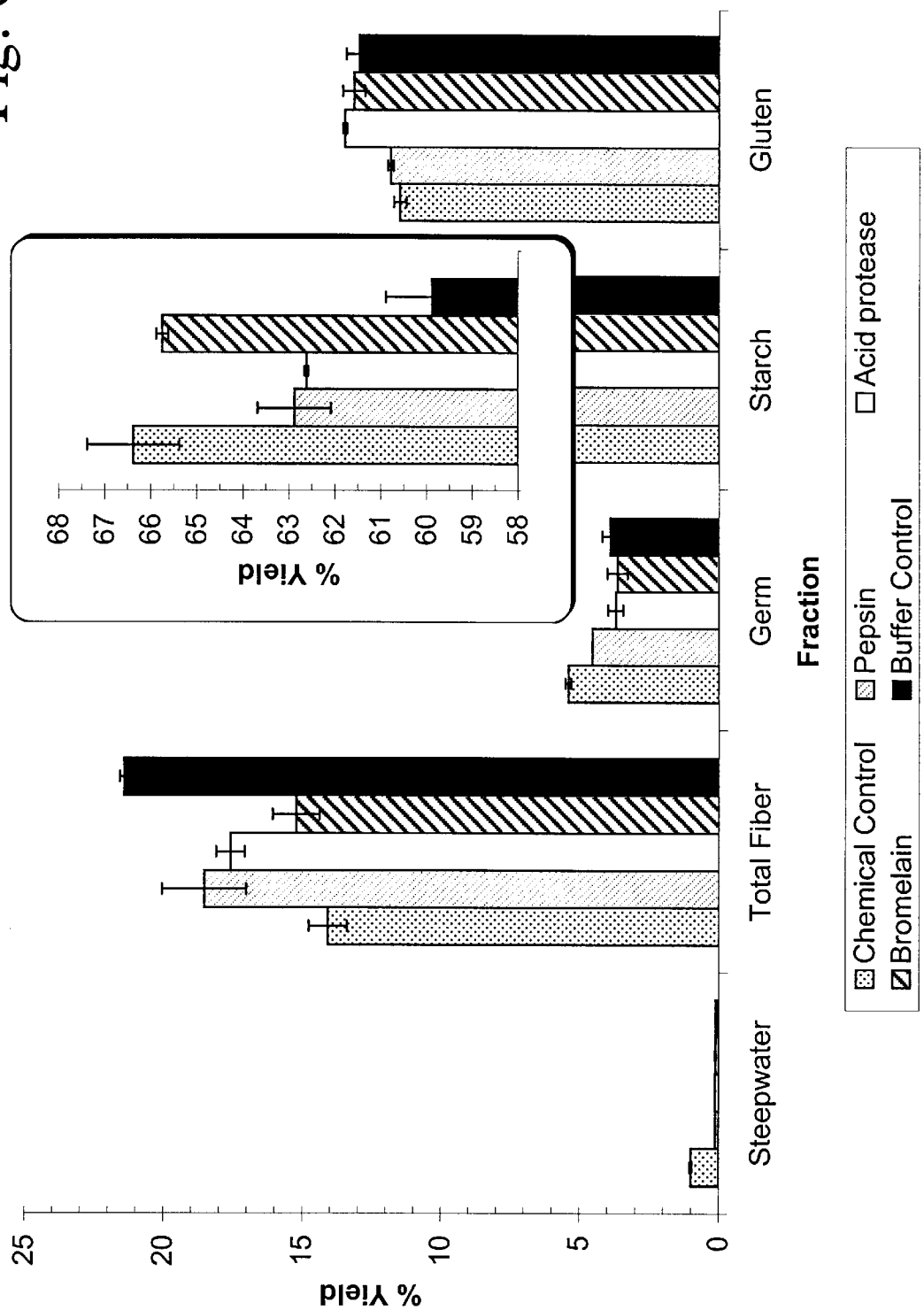
FIG. 6 shows a comparison of fraction yields from corn samples steeped using proteases, normal chemicals (chemical control; $SO_2$ at 2000 ppm and 0.55% lactic acid) and buffer alone (buffer control; 0.05 M acetate buffer, pH 4.0); error bars represent±one standard deviation from a duplicate average (quadruplicate for controls).

Results of Two-Stage Procedure with Proteases:

Three different proteases (pepsin, acid protease or bromelain) were tested individually and in combination with other hydrolases (cellulases, xylanases and β-glucanase) using the two-stage procedure. Fraction yields for proteases without additional enzymes are shown in FIG. 6. Pepsin and the acid protease showed a significant improvement in starch yields over the buffer control; however, bromelain showed the largest improvement. There was also a significant decrease in the total fiber yield from the three proteases tested as compared to the total fiber yield from the buffer control. There was no significant difference in the fiber yield between the chemical control and the bromelain treated sample. Mixtures of the proteases with the other hydrolases showed no additional improvement in starch yields over the use of protease alone; however, changes in the fiber and/or gluten fractions were observed.

Figure 7:
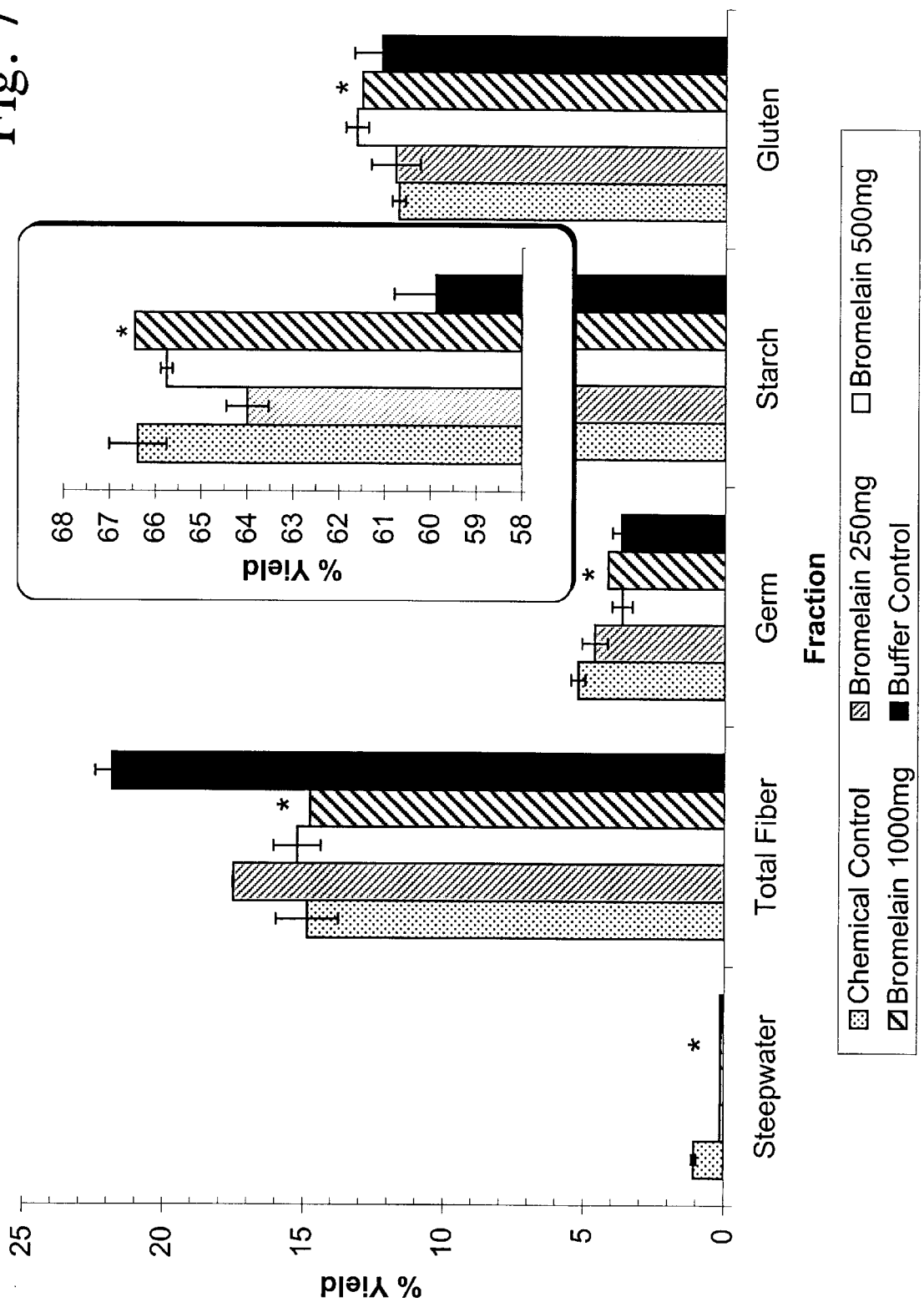
FIG. 7 shows a comparison of fraction yields from corn samples steeped using three concentrations of Bromelain, normal chemicals (chemical control; $SO_2$ at 2000 ppm and 0.55% lactic acid) and buffer alone (buffer control; 0.05 M acetate buffer, pH 4.0); error bars represent±one standard deviation from a duplicate average (quadruplicate for controls).

Results Showing Effect of Bromelain Concentration:

Using the two-stage procedure, the effects of bromelain concentration on starch recovery were determined. Three levels of enzyme were evaluated (250, 500 and 1000 mg per 100 g corn). Fraction yields are shown in FIG. 7. All levels tested showed improvements in starch yields over the buffer controls. Significant differences were observed between the 250 and 500 mg treatments. There was only one replicate for the 1000 mg sample.

Figure 8:
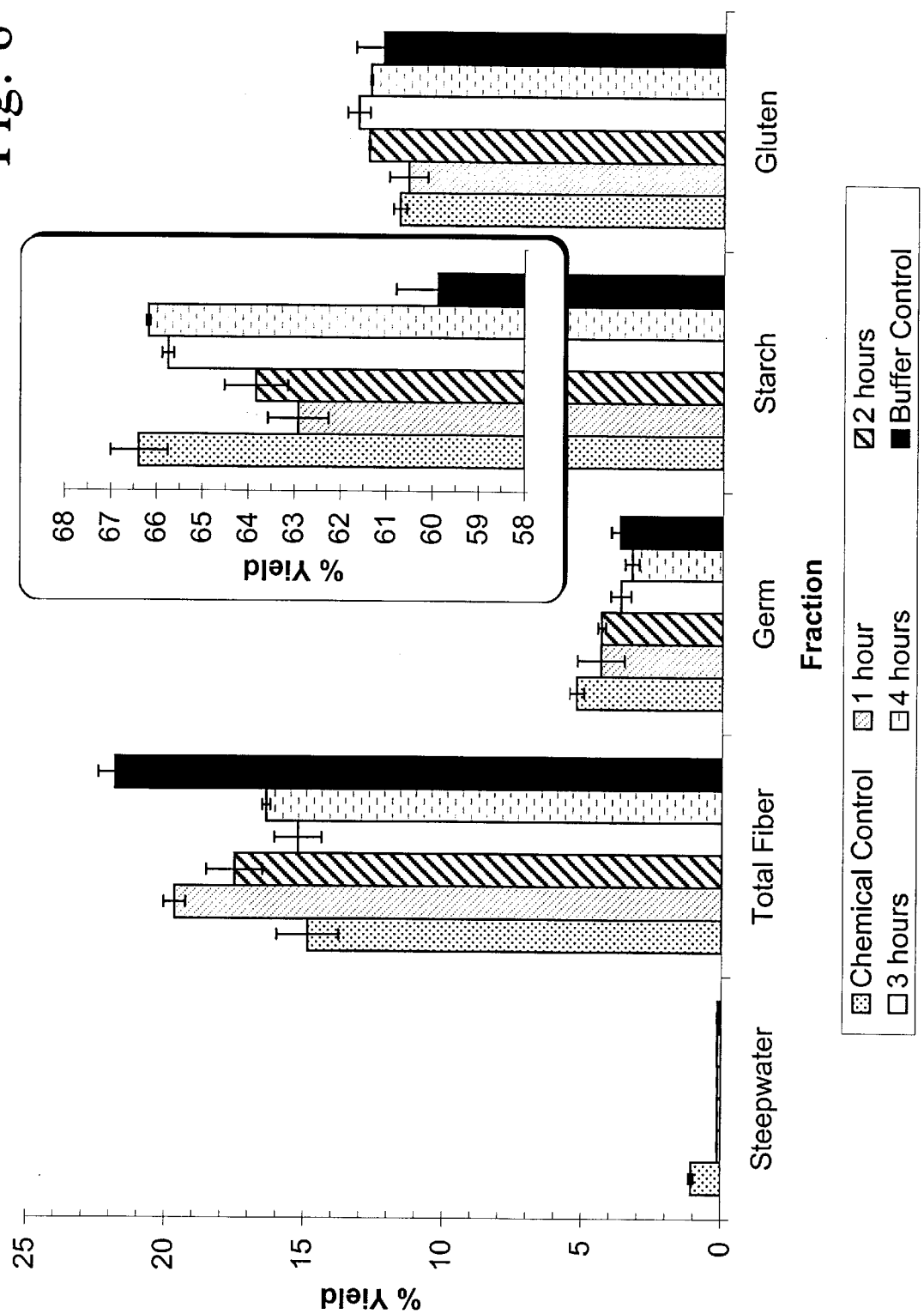
FIG. 8 shows a comparison of fraction yields from corn samples steeped using bromelain for 1, 2, 3 & 4 hours of incubation, normal chemicals for 3 hours (chemical control; $SO_2$ at 2000 ppm and 0.55% lactic acid) and buffer alone for 3 hours (buffer control; 0.05 M acetate buffer, pH 4.0); error bars represent±one standard deviation from a duplicate average (quadruplicate for controls).

Results of Time Course of Bromelain Treatment:

Using the two-stage procedure and the 500 mg application level of bromelain, a time course for the treatment was done. Samples were soaked for 3 hours in water ($1^{st}$ step of modified procedure), followed by coarse grinding and enzymatic treatment for 1, 2, 3 or 4 hours prior to milling ($2^{nd}$ step of modified procedure). The fraction yields are shown in FIG. 8. The results clearly show a progressive increase in starch yields and a general lowering of total fiber with increased incubation times.

Figure 9:
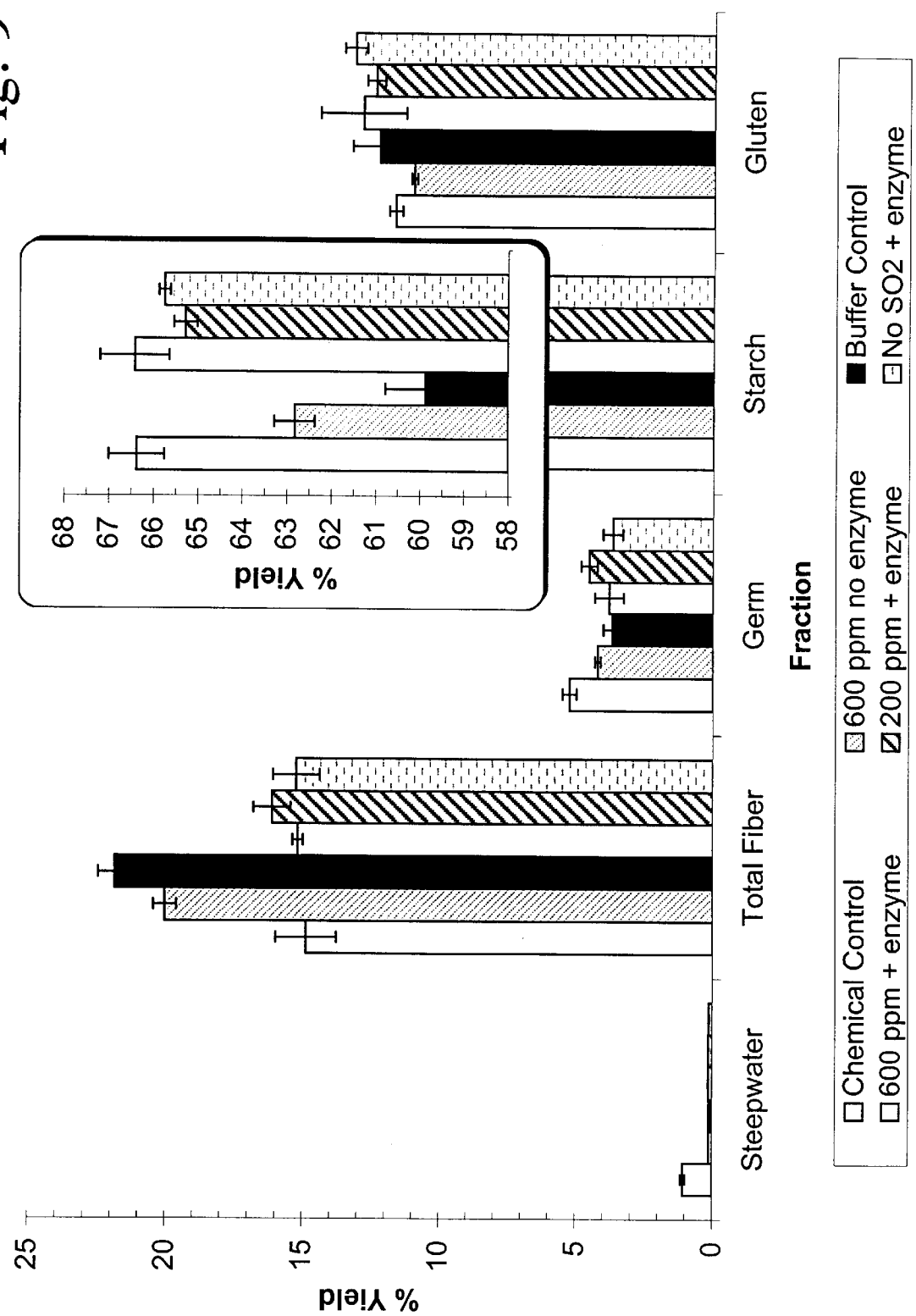
FIG. 9 shows a comparison of fraction yields from corn samples steeped using normal chemicals (chemical control; $SO_2$ at 2000 ppm and 0.55% lactic acid), decreased $SO_2$ without enzyme (600 ppm no lactic acid), decreased $SO_2$ with 500 mg bromelain (200 and 600 ppm no lactic acid), bromelain (500 mg) without $SO_2$ or lactic acid and buffer alone (buffer control; 0.05 M acetate buffer, pH 4.0); error bars represent±one standard deviation from a duplicate average (quadruplicate for controls).

Results Showing the Effect of Sulfur Dioxide on Enzyme Treatments:

Sulfur dioxide ($SO_2$) is used in corn wet-milling plants to control microbial growth. To determine if sulfur dioxide levels (200–600 ppm) lower than those used commercially (1000–2000 ppm) could be added to inhibit microbial growth without effecting enzyme activity during the modified milling process, samples were processed with and without sulfur dioxide added during the incubation stage. The results are shown in FIG. 9. Samples treated with 600 ppm sulfur dioxide alone showed a small increase in starch yields compared to the buffer controls; however, the total fiber yield was significantly elevated and starch yields were significantly lower than for the bromelain treated samples as well as the chemical controls. Samples that were treated with bromelain alone showed improved starch yields when compared to the starch yields of the buffer controls, as in previous experiments. Addition of both bromelain and sulfur dioxide showed a further improvement in starch yields compared to the controls at the 600 ppm level; however, at the 200 ppm level there was no additional improvement.

Figure 3:
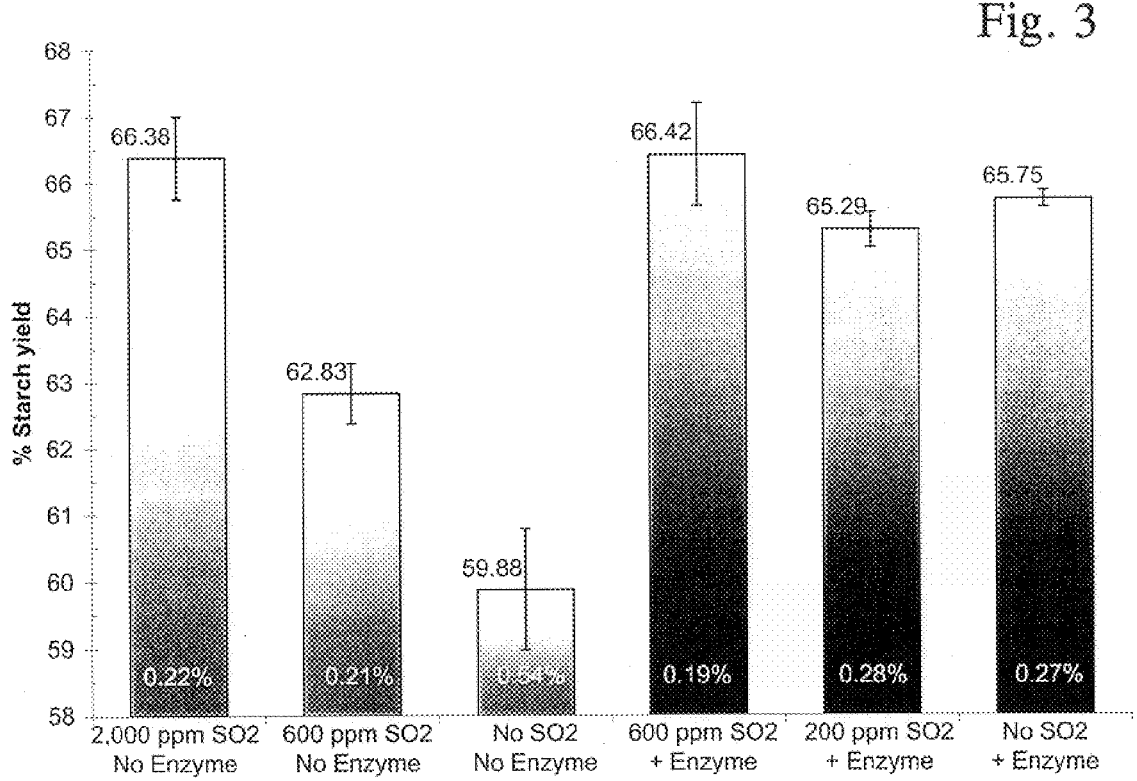
FIG. 3 shows a comparison of starch yields from corn samples steeped using the two step procedure with conventional steeping chemicals ($SO_2$ at 2000 ppm and lactic acid), decreased $SO_2$ without enzyme (600 ppm no lactic acid), decreased $SO_2$ (200 and 600 ppm) with enzyme and controls (no $SO_2$ with enzyme and no $SO_2$ without enzyme), error bars represent±one standard deviation from a duplicate average, percent values indicate average protein content of sample.
Figure 4:
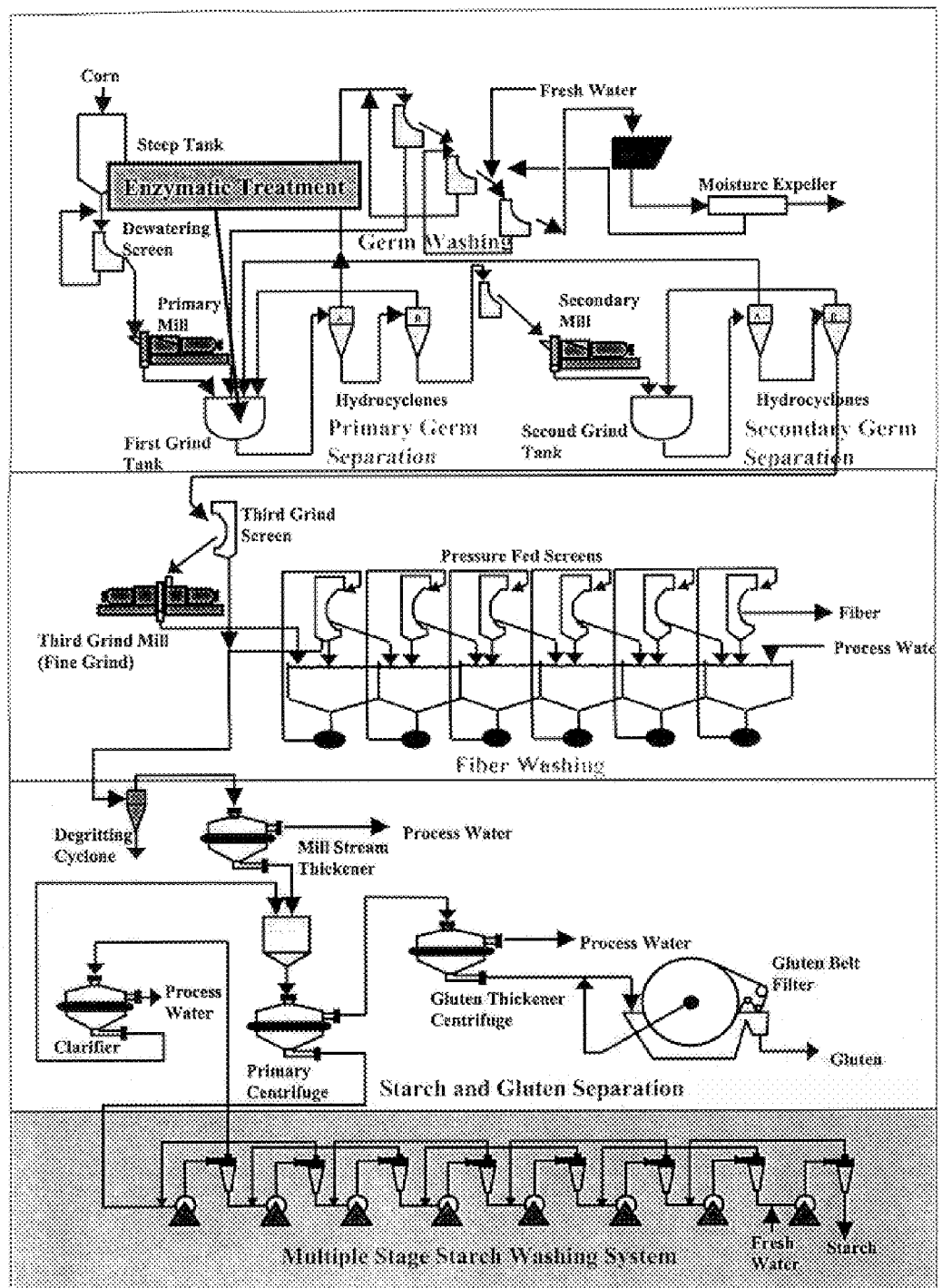
FIG. 4 shows a general diagram showing conventional corn wet-milling process and location of the new enzymatic treatment.

Results Regarding Protein in Starch:

The residual protein contents in the starch samples obtained from the milling studies was determined for bromelain treated and sulfur dioxide treated samples. FIG. 3 shows the results of the starch yields as well as the percentage of protein determined for each starch fraction. The protein content of the sulfur dioxide treated and enzyme treated samples were all significantly lower than the buffer controls (no enzyme, no $SO_2$). The differences between the individual samples, however, were not significant enough to make any additional conclusions about the effectiveness of protein removal using protease treatments. The combined effect of low level sulfur dioxide plus the application of the protease enzyme does appear to be more effective at lowering the final protein content of the produced starch than either treatment alone.

Results of 10× Scale Procedure:

Conventional corn wet milling was done using the 1 Kg scale laboratory corn wet milling procedure. (Eckhoff, S. R., et al., Cereal Chem., 69:191–197 (1993)). The enzymatic milling procedure was done using a 10× scale procedure of the two-stage modified 100 g wet milling procedure. Corn samples (1000 g) were soaked in 2 L of water at 55° C. for 3 hours. The water was drained and the corn blended using 1.5 L of fresh water. The slurry was transferred to a stainless steel bucket and buffer (final concentration, 0.05 M acetate buffer, pH 5.0) and 5 g bromelain were added. The slurry was incubated for 3 hours at 48° C. in a water bath and continually mixed using a mechanical stirrer. Further separations and processing were done according to Eckhoff, S. R., et al., Cereal Chem., 69:191–197 (1993). Fraction yields from the Kg procedure using bromelain showed a significant increase in starch and gluten recovery when compared to yields from the conventional milling samples. Soak water dry solids from the bromelain treatments were greatly decreased when compared to the conventional milling yields.

To overcome the problem of enzyme penetration into the intact endosperm, our approach was to use a two-stage steeping system. The first stage is to hydrate the corn kernel in water (no steeping chemicals added) for several hours (e.g., 3 h) so that the germ is completely hydrated and becomes pliable enough that it does not break when the corn is coarsely ground. The second part of our steeping system involves treating the coarsely ground corn slurry with enzyme (e.g., protease). After treatment, the corn will be milled using the normal corn wet-milling methods. This approach removes the diffusion barriers and allows the enzymes to penetrate the corn endosperm and react with the protein substrates.

The enzyme preparations that gave the most significant improvements in starch yields using the two-stage procedure were the proteases. The proteases selected for testing were chosen based on their pH optima, temperature stability, and the enzyme's potential for retaining activity in the presence of $SO_2$ (cysteine proteases). The retention of activity in the presence of sulfur dioxide was considered very important since it is likely that low-level addition of $SO_2$ will still be desired to prevent microbial contamination. Other proteases could be useful in the absence of sulfur dioxide or with the use of another antimicrobial compound.

The proteases alone were found to be as effective or more effective than when used in mixtures with other hydrolases (FIG. 6). This was somewhat surprising since it was believed that hemicellulose degrading enzymes would help release the bound starch from the fiber. The starch yields from bromelain treated samples were significantly higher than the yields from pepsin or acid protease treated samples. This was likely due at least in part to the non-optimal pH conditions used for pepsin and acid protease. It was necessary to use a compromised pH (where all are active but not necessarily optimally) to avoid having an excessive number of control samples.

Bromelain was selected for additional studies to determine if yields could be improved further and to determine the minimum amount of enzyme necessary to maintain starch yield. Three different levels of bromelain (250, 500 and 1000 mg using 3 h soak and 3 h incubation) were tested and 4 incubation times (1, 2, 3 and 4 h using 500 mg bromelain and a 3 h soak) (FIGS. 7 & 8). The 250 mg bromelain addition gave starch yields higher than the starch yields given by pepsin or acid protease tested previously (FIG. 6), but was several percent lower than the starch yields from the chemical control samples. The starch yield was higher than the 500 mg treated samples incubated for 2 h or less, but not after longer incubations. Incubations longer than 3 h were not tested using the 250 mg treatment; however, it is likely that yields would eventually reach chemical control yields provided the enzyme is not inactivated.

A difference between the starch yields for the 500 and the 1000 mg bromelain treated samples was observed but statistical significance could not be assigned (only 1 data set for the 1000 mg treated sample). The total fiber yields were not found to be significantly different between the 500 and the 1000 mg bromelain treated samples. Although not tested, it is unlikely that further gains could be made through the addition of additional bromelain.

The time course analysis (FIG. 8) showed greater starch yields with increasing time of incubation; however, the change per unit time decreases steadily, indicating a maximum value for starch yields. When we plotted the data on an XY graph and calculated the $2^{nd}$ order best-fit equation, the maximum was 66.3 percent which is approximately equal to the chemical control yields.

Figure 10:
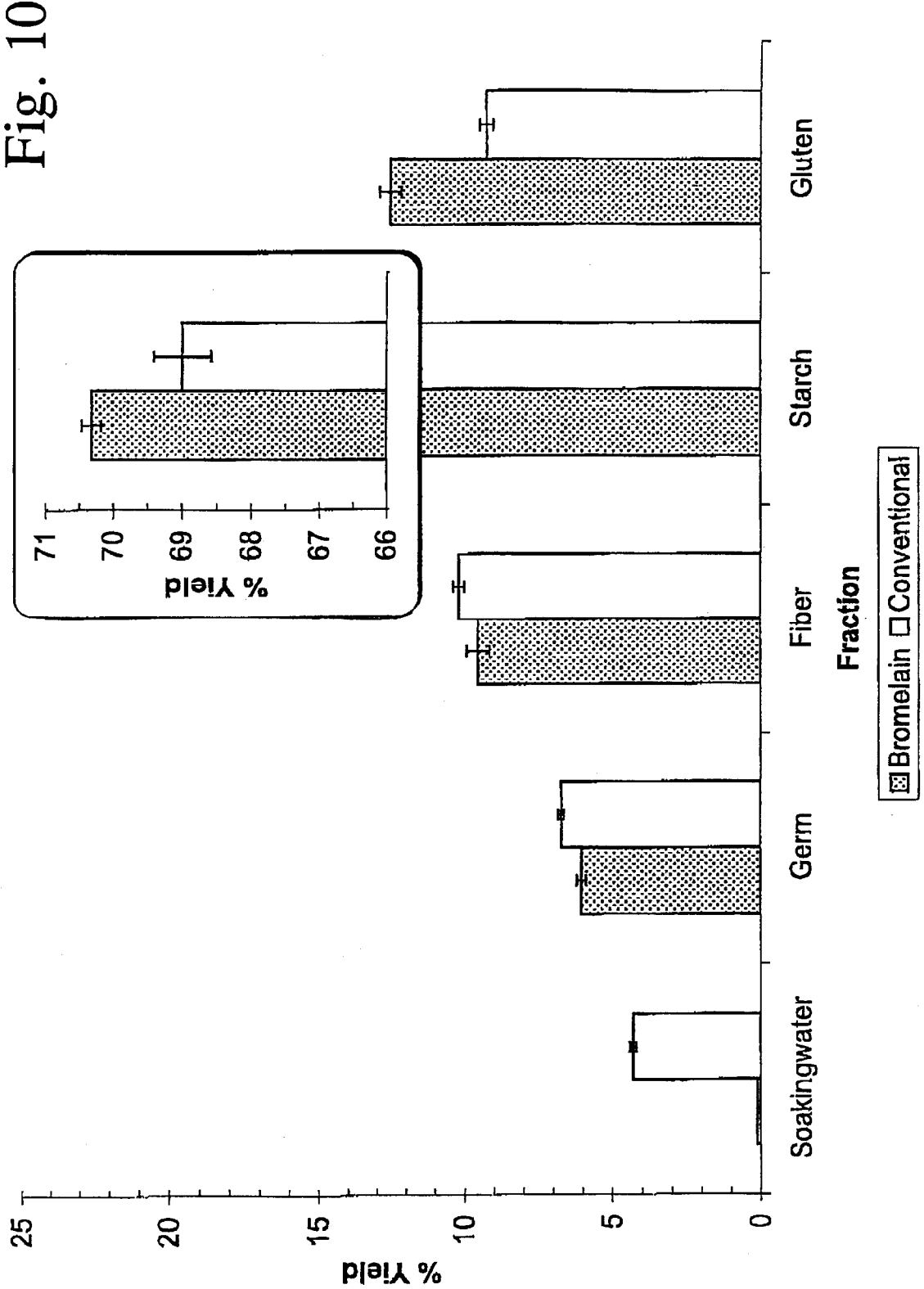
FIG. 10 shows a comparison of fraction yields from corn samples processed using a Kg corn wet milling procedure. Conventionally processed samples were steeped using $SO_2$ at 2000 ppm and 0.55% lactic acid. Bromelain treatments were done with 3 hours of soaking and 3 hours of incubation using 5 g of bromelain (500 mg/100 g corn) with 0.05 M acetate buffer, pH 5.0. Error bars represent±one standard deviation from a duplicate average.

The final series of experiments was done to determine the effects of low-level sulfur dioxide addition on the process during the incubation step. Microbial contamination could be a potential problem during the enzyme incubation stage of the processing. Sulfur dioxide addition at levels of 200–600 ppm (depending on pH) could be effective at inhibiting microbial growth (Block, R. L., Antimicrobials in Food Sanitation and Preservation, pages 814–815, IN: Disinfection, Sterilization, and Preservation, $4^{th}$ ed., 1995, Lea & Febiger, Philadelphia; Lewis, R. J., Food Additives Handbook, 1989, pages 412–413, Van Nostrand Reinhold, New York). As expected, we found that sulfur dioxide addition (without enzyme or lactic acid) gave some improvement in starch yields over controls (buffer only) (FIG. 9 & 10). The enzyme treated samples all showed greater improvements in starch yields over the sulfur dioxide only treated samples. The combination of sulfur dioxide (600 ppm) with the enzyme addition showed the greatest improvement and was on average better than the chemical control samples. Protein determinations were made on the starch samples produced (FIG. 10) to determine if the enzymatic treatments were adequately removing protein from the starch. The control starch sample (no sulfur dioxide and no enzyme) showed an average protein content of 0.54% and individual values as high as 0.7%, well above the 0.3% acceptance level. The enzyme treated starch samples were all below 0.28% and as low as 0.19% for the combined sulfur dioxide bromelain treatment. It was clear from the data that the addition of sulfur dioxide to the enzyme incubation did not have a negative effect on the enzymatic activity, but did give a slight improvement over using the enzyme alone.

Additional proteases that could be used in this process would need to possess activity and stability under the specific conditions used. These proteases would also need to hydrolyze the proteins surrounding the starch granules. Such enzymes would have specificity toward peptide linkages in glutelins, zein and other minor corn endosperm proteins. Resulting peptides would then be separated during processing. The reaction conditions would need to consider enzyme concentration, pH, temperature, sulfur dioxide tolerance (if used), and other enzyme specific factors such as mineral or cofactor requirement. Further improvements in starch recovery may be made through the selection of other enzymes.

Our process presents a number of potential benefits that have not been specifically addressed by the presented research, but are likely outcomes of its application: (1) The shorter steeping times could decrease the energy cost and the capitol investment in the steeping tanks. (2) The shorter processing times could increase plant capacity. (3) The process could potentially use broken as well as unbroken grains by grinding and adding them directly to the incubation tank or by soaking for a decreased time (relative to intact kernels) before adding to the milling stream. This would result in increased primary product output (starch) for the same input of corn. (4) The soak water from the modified process contains relatively low dissolved solids when compared to the conventional light steep water (approximately 90% less). This water could potentially be recycled by using membrane filtration eliminating the need and expense for evaporators.

All of the references cited herein are incorporated by reference in their entirety.

Thus, in view of the above, the present invention concerns (in part) the following:

A method for obtaining starch from maize, involving soaking maize kernels in water to produce soaked maize kernels, grinding the soaked maize kernels to produce a ground maize slurry, and incubating the ground maize slurry with enzyme.

The above method, wherein the soaking is for about 1 to about 6 hours or for about 2 to about 4 hours or for about 3 hours.

The above method, wherein the soaking is at about 45° to about 60° C. or at about 48° to about 52° C. or at about 45° to about 50° C. or at about 48°.

The above method, wherein the incubating is for about 0.5 to about 6 hours or for about 1 to about 4 hours or for about 3 hours.

The above method, wherein the incubating is at about 20° to about 70° C. or at about 40° to about 55° C. or at about 48°.

The above method, wherein the method (soaking, grinding, incubating with enzyme) utilizes less than about 2500 ppm $SO_2$ (e.g., less than 2500 ppm $SO_2$) or less than about 2000 ppm $SO_2$ (e.g., less than 2000 ppm $SO_2$) or less than about 1900 $SO_2$ (e.g., less than 1900 ppm $SO_2$) or less than about 1800 $SO_2$ (e.g., less than 1800 ppm $SO_2$) or less than about 1700 $SO_2$ (e.g., less than 1700 ppm $SO_2$) or less than about 1600 $SO_2$ (e.g., less than 1600 ppm $SO_2$) or less than about 1500 $SO_2$ (e.g., less than 1500 ppm $SO_2$) or less than about 1400 $SO_2$ (e.g., less than 1400 ppm $SO_2$) or less than about 1300 $SO_2$ (e.g., less than 1300 ppm $SO_2$) or less than about less than 1200 $SO_2$ (e.g., less than 1200 ppm $SO_2$) or less than about 1100 $SO_2$ (e.g., less than 1100 ppm $SO_2$) or less than about 1000 $SO_2$ (e.g, less than 1000 ppm $SO_2$) or less than about 900 $SO_2$ (e.g., less than 900 ppm $SO_2$) or less than about 800 $SO_2$ (e.g, less than 800 ppm $SO_2$) or less than about 700 $SO_2$ (e.g., less than 700 ppm $SO_2$) or less than about 600 $SO_2$ (e.g., less than 600 ppm $SO_2$) or less than about 500 $SO_2$ (e.g., less than 500 ppm $SO_2$) or less than about 400 $SO_2$ (e.g., less than 400 ppm $SO_2$) or less than about 300 $SO_2$ (e.g., less than 300 ppm $SO_2$) or less than about 200 $SO_2$ (e.g., less than 200 ppm $SO_2$) or less than about 100 $SO_2$ (e.g, less than 100 ppm $SO_2$) or less than about 50 $SO_2$ (e.g., less than 50 ppm $SO_2$) or about 0 ppm $SO_2$ (e.g., 0 ppm $SO_2$).

The above method, wherein the enzyme is a protease (e.g., Bromelain).

The above method, wherein the concentration of the enzyme is about 1000 mg (e.g., 1000 mg) per 100 g of maize or about 500 mg (e.g., 500 mg) per 100 g of maize or about 250 mg (e.g., 250 mg) per 100 g of maize or about 100 mg (e.g., 100 mg) per 100 g of maize or about 50 mg (e.g., 50 mg) per 100 g of maize.

The above method further involving grinding and de-germing of the ground maize slurry after incubating with said enzyme.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for obtaining starch from maize, comprising soaking maize kernels in water for about 1 to about 6 hours to produce soaked maize kernels, grinding said soaked maize kernels to produce a ground maize slurry, and incubating said ground maize slurry with protease, wherein said method utilizes less than about 600 ppm $SO_2$.

2. The method according to claim 1, wherein said soaking is for about 2 to about 4 hours.

3. The method according to claim 1, wherein said soaking is for about 3 hours.

4. The method according to claim 1, wherein said soaking is at about 45° to about 60° C.

5. The method according to claim 1, wherein said soaking is at about 45° to about 50° C.

6. The method according to claim 1, wherein said soaking is at about 48°.

7. The method according to claim 1, wherein said incubating is for about 0.5 to about 6 hours.

8. The method according to claim 1, wherein said incubating is for about 1 to about 4 hours.

9. The method according to claim 1, wherein said incubating is for about 3 hours.

10. The method according to claim 1, wherein said incubating is at about 20° to about 70° C.

11. The method according to claim 1, wherein said incubating is at about 40° to about 55° C.

12. The method according to claim 1, wherein said incubating is at about 48°.

13. The method according to claim 1, wherein said method utilizes less than about 100 ppm $SO_2$.

14. The method according to claim 1, wherein said method utilizes about 0 ppm $SO_2$.

15. The method according to claim 1, wherein said protease is Bromelain.

16. The method according to claim 1, wherein the concentration of said protease is about 1000 mg per 100 g of maize.

17. The method according to claim 1, wherein the concentration of said protease is about 500 mg per 100 g of maize.

18. The method according to claim 1, wherein the concentration of said protease is about 250 mg per 100 g of maize.

19. The method according to claim 1, wherein the concentration of said protease is about 100 mg per 100 g of maize.

20. The method according to claim 1, wherein the concentration of said protease is about 50 mg per 100 g of maize.

21. The method according to claim 1, further comprising grinding and de-germing of said ground maize slurry after said incubating with said protease.

22. The method according to claim 1, consisting essentially of soaking maize kernels in water for about 1 to about 6 hours to produce soaked maize kernels, grinding said soaked maize kernels to produce a ground maize slurry, and incubating said ground maize slurry with protease, wherein said method utilizes less than about 600 ppm $SO_2$.

* * * * *